(12) United States Patent
D'Aloia et al.

(10) Patent No.: US 9,404,918 B2
(45) Date of Patent: Aug. 2, 2016

(54) DETECTION OF COMPOUNDS IN A DRIED FLUID SPOT BY DIRECT MALDI/MS

(71) Applicant: Zentech, Angleur (BE)

(72) Inventors: Maria D'Aloia, Vottem (BE); Nicolas Smargiasso, Liège (BE); Delphine Debois, Liège (BE); Edwin De Pauw, Liège (BE)

(73) Assignee: Zentech, Angleur (BE)

( * ) Notice: Subject to any disclaimer, the term of this patent is extended or adjusted under 35 U.S.C. 154(b) by 0 days.

(21) Appl. No.: 14/775,088

(22) PCT Filed: Mar. 13, 2014

(86) PCT No.: PCT/EP2014/054998
§ 371 (c)(1),
(2) Date: Sep. 11, 2015

(87) PCT Pub. No.: WO2014/140202
PCT Pub. Date: Sep. 18, 2014

(65) Prior Publication Data
US 2016/0047799 A1    Feb. 18, 2016

Related U.S. Application Data

(60) Provisional application No. 61/781,316, filed on Mar. 14, 2013.

(30) Foreign Application Priority Data

Mar. 14, 2013  (EP) .................................. 13159111

(51) Int. Cl.
*G01N 33/52* (2006.01)
*G01N 33/92* (2006.01)
*G01N 33/68* (2006.01)
*G01N 33/50* (2006.01)
(Continued)

(52) U.S. Cl.
CPC .............. *G01N 33/523* (2013.01); *G01N 33/50* (2013.01); *G01N 33/52* (2013.01); *G01N 33/6851* (2013.01); *G01N 33/492* (2013.01); *G01N 33/92* (2013.01); *G01N 2560/00* (2013.01); *H01J 49/0027* (2013.01); *Y10T 436/24* (2015.01)

(58) Field of Classification Search
CPC ..... G01N 33/48; G01N 33/49; G01N 33/492; G01N 33/66; G01N 33/68; G01N 33/6848; G01N 33/6851; G01N 33/92; H01J 49/00; H01J 49/0027; H01J 49/26; Y10T 436/143333; Y10T 436/24; Y10T 436/25; Y10T 436/25375; Y10T 436/255
USPC ........... 436/63, 71, 86, 89, 94, 173, 174, 177, 436/178; 250/281, 282; 435/29
See application file for complete search history.

(56) References Cited

PUBLICATIONS

Meesters et al. Analytical Bioanalytical Chemistry, vo. 398, 2010, pp. 319-328.*

(Continued)

*Primary Examiner* — Maureen Wallenhorst
(74) *Attorney, Agent, or Firm* — Norris McLaughlin & Marcus, P.A.

(57) ABSTRACT

It is provided a method for detection and/or quantification of at least one molecule presents in blood by a MALDI-MS analysis of a dried fluid spot without the presence of any digestion step or liquid extraction step, which permits to further analyze the physical distribution of at least one molecule within a dried fluid spot.

15 Claims, 5 Drawing Sheets

Figure 1:
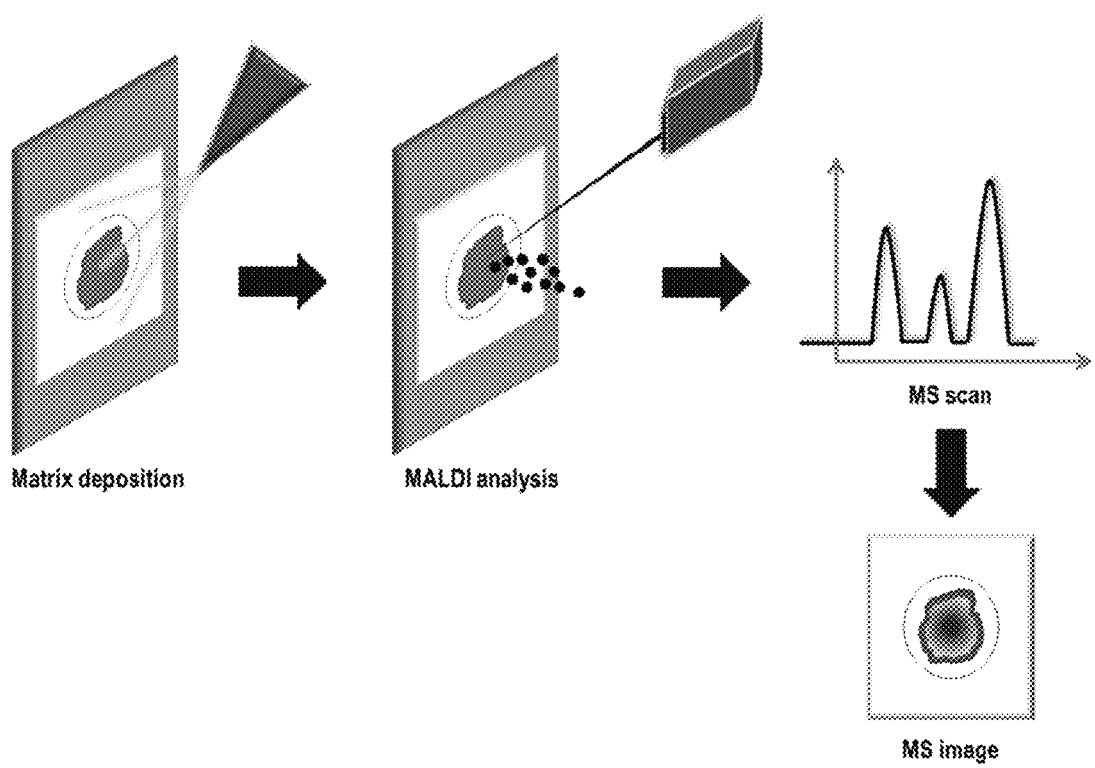

(51) Int. Cl.
*G01N 33/49* (2006.01)
*H01J 49/00* (2006.01)

(56) References Cited

PUBLICATIONS

Kertesz et al. Journal of Mass Spectrometry, vol. 45, Dec. 17, 2009, pp. 252-260.*
Schreiner et al. Electrophoresis, vol. 17, 1996, pp. 954-961.*
Stubiger et al. Analytical Chemistry, vol. 82, No. 13, Jul. 1, 2010, pp. 5502-5510.*
International Search Report for Application No. PCT/EP2014/054998 dated May 15, 2014.
Deglon, et al., "Direct Analysis of Dried Blood Spots Coupled With Mass Spectrometry: Concepts and Biomedical Applications," Analytical and Bioanalytical Chemistry; Mar. 2012; vol. 402, No. 8; pp. 2485-2498; Geneva, Switzerland.
De Hoffmann, et al., "Chapter 1.8 Matrix-Assisted Laser Desorption Ionization," Mass Spectrometry: Principles and Applications, 3rd Edition, John Wiley & Sons Ltd., Sep. 2007, pp. 33-41.
Price, Phil, "Standard Definitions of Terms Relating to Mass Spectometry," J. Am. Soc. Mass Spectrom, 1991, vol. 2; pp. 336-348; South Carleston, West Virginia.
Fuchs, et al., "The Phosphatidycholine/lysophoisphatidylcholine Ratio in Human Plasma is an Indicator of the Severity of Rheumatoid Arthritis: Investigations by P NMR and MALDI-TOF MS," Clinical Biochemisry, Oct. 2005, vol. 38, No. 10; pp. 925-933, Leipzig, Germany.
Stuebiger, et al., "Targeted Profiling of Atherogenic Phospholipids in Human Plasma and Lipoproteins of Hyperlipidemic Patients Using MALDI-QIT-TOF-MS/MS," Atherosclerosis, Sep. 2012; vol. 224, No. 1; pp. 177-186; Vienna, Austria.
Meesters, et al., "Ultrafast and High-Throughout Mass Spectrometric Assay for Therapeutic Drug Monitoring of Antiretroviral Drugs in Pediatric HIV-1 Infection Applying Dried Blood Spots," Analytical and Bioanalytical Chemistry; Sep. 2010; vol. 398, No. 1; pp. 319-328; Rotterdam, The Netherlands.
Razunguzwa, et al., "Analysis of Verapamil on Dried Blood Spot (DBS) Cards by LAESI-MS," Protea Biosciences, Inc.,; 2011, pp. 1-3; United States of America.
Kertesz, et al., "Fully Automated Liquid Extraction-Based Surface Sampling and Ionization Using a Chip-Based Robotic Nanoelectrospray Platform," Journal of Mass Spectrometry; Mar. 2010; vol. 45, No. 3; pp. 252-260; Oak Ridge, Tennessee.
Schreiner, et al., "Ultraviolet Matrix Assisted Laser Desorption Ionization-Mass Spectrometry of Electroblotted Proteins," Electropharesis, Wiley Interscience; May 1, 1996; vol. 17, No. 1; pp. 954-961, Weinheim, Germany.
Musapelo, et al., "Particle Formation in Ambient MALDI Plumes," Analytical Chemistry; Sep. 1, 2011; vol. 83, No. 17, pp. 6601-6608; Baton Rouge, Louisiana.
Stuebiger, et al., "Analysis of Oxidized Phospholipids by MALDI Mass Spectrometry Using 6-Aza-2-thiothymine Together With Matrix Additives and Disposable Target Surfaces," Analytical Chemistry; Jul. 1, 2010; vol. 82, No. 13; pp. 5502-5510; Vienna, Austria.

* cited by examiner

DETECTION OF COMPOUNDS IN A DRIED FLUID SPOT BY DIRECT MALDI/MS

This application is a 371 application of PCT/EP2014/054998 filed Mar. 13, 2014, which claims foreign priority benefit under 35 U.S.C. §119 of European Application No. EP 13159111.7 filed Mar. 14, 2013, and claims the benefit under 35 U.S.C. 119(e) of U.S. Provisional Patent Application No. 61/781,316, filed on Mar. 14, 2013, which is incorporated herein by reference in its entirety.

FIELD OF THE INVENTION

The invention relates to a method of detection of at least one compound present in biological fluids. More particularly, the invention relates to a method of detection and/or identification of at least one compound present in a dried fluid spot. The invention also relates to a method for analyzing the spatial distribution of a compound in a dried fluid spot. The present application describes new methods for dried fluid spot analyses.

DESCRIPTION OF PRIOR ART

Fluid analyses are currently mainly performed on liquid samples. Such samples do not allow an easy transportation and the integrity of molecular compounds cannot be preserved over a long period of time. With the purpose to permit an easiest transportation and a longer preservation, fluids may be dried on suitable supports. For example, dried blood spot (or DBS) is a minimal blood sampling technique that consists in blotting at least one droplet of blood onto a paper support. Generally, the paper support is specially designed to absorb the blood droplet for further analysis. The blood spot is allowed to air dry a couple of hours at room temperature before to be sent to analysis laboratories. Low amount of blood sample and easy handling of specimens have made the success of the DBS sampling technique. Moreover, it allows a simplified storage and cheap shipping. Its success started in the 1960s, when Dr. Robert Guthrie developed an assay for the detection of phenylketonuria. Since then, the 'Guthrie card' has been worldwide adopted for newborn screening of infants. Advantages of blood sampling with a cellulosic support (less invasive method using lower blood volume) were particularly suitable for pediatric patients but are also attractive for preclinical and clinical studies (3R compliance: replacement, refinement and reduction). Currently, the use of dried spot sampling technic is extended to other biological fluids, such as serum, plasma or urine.

For example, both newborn screening and pharmaceutical activities have adopted the mass spectrometry (or MS) technology for dried blood spot analysis. Until recently, several steps of extraction in a liquid medium and separation are still necessary; leading to a long preparation of the sample before MS analysis may be performed. The liquid extraction of a punch taken from a dried blood spot sample is generally performed using a mixture of aqueous and organic solvents and is followed by Liquid Chromatographic (LC) separation. Because of the presence of a step of liquid extraction and/or a step of separation, contamination of the sample and/or damage of the compounds present in the sample may occur during one of these steps. To circumvent these problems of sample preparation and manipulation, which are of primary importance in the diagnostic and pharmaceutical fields, novel and direct techniques were developed (reviewed in Deglon et al., 2012 [Anal Bioanal Chem 2012, 402:2485-2498]). Technical developments were mainly focused on rapid analysis of DBS by either direct elution (e.g. on-line liquid extraction) or by direct desorption/ionization. The latter method is the fastest solution (no pretreatment is required), particularly suitable for high throughput dried fluid spot analysis. In this context, several ambient MS methods, developed from different basic ionization techniques, were launched: Desorption electrospray ionization (DESI) and Paper Spray Ionization (PSI) in electrospray ionization (ESI), Direct Analysis in Real Time (DART) in gas discharged ionization (GDI) and Atmospheric Pressure Thermal Desorption Chemical Ionization (APT-DCI) in electron ionization (EI).

These MS methods are used to analyze different dried fluid spots but major limitations are present. For example, analyte distribution in dried blood spot may be affected by several factors such as blood spot volume, hematocrit level and diffusion properties (chromatographic effect). Analyte assay by direct desorption/ionization may be affected by these factors. Analyte distribution imaging is a useful method to direct the development of these analyte assays. However, analyte distribution imaging in dried blood spot has been done by. Autoradiography sensitivity and resolution are not yet sufficient for a reliable analysis. Hence, direct desorption/ionization methods to analyze dried spot sample are limited because of a poor sensitivity and/or a poor resolution of imaging method, leading to imprecisions in the analyte detection. Sample preparation and subsequent analysis remain fundamental issues that limit the use of these methods in the field of dried spot analysis.

Hence, there is a need for a simple, fast and reliable MS method to detect a compound present in a dried spot without pretreatment. Moreover, there is also a need for a MS method allowing compounds imaging in dried spot without the use of specific labels and with a high sensitivity and a high mass resolution, without being too sensitive to biological contaminants.

SUMMARY OF THE INVENTION

Hence in this context, the object of the present invention is to solve at least partially the problems of the state-of-the-art by providing a method for the detection of at least one compound present in a fluid sample, preferably without a liquid extraction step, eventually with a blotting step that keeps the spatial distribution of the compounds present in a dried spot, and allowing a further determination of their spatial distribution by molecular imaging tools.

According to a first aspect of the invention, there is provided a method for detecting at least one compound present in biological fluids, said method comprising the following steps:
  a. providing at least one dried fluid spot on a support,
  b. fixing at least a part of said dried fluid spot on said support on a conductive surface,
  c. providing an aqueous or organic solution of a UV-light-absorbing compound,
  d. depositing said UV-light-absorbing compound on at least a part of said dried fluid spot on said support fixed on said conductive surface,
  e. subjecting at least an area of said dried fluid spot on a support to a Matrix Assisted Laser Desorption/Ionization process to produce ions,
  f. acquiring a full scan mode mass spectrum of said ions by a mass spectrometer analyzer and,
  g. determining the presence of the at least one compound by analyzing the full scan mode mass spectrum.

Such method allows a fast and reliable detection and visualization of at least one compound present in a dried fluid spot, without any pretreatment step before an analysis by MS.

The present inventors have found that the direct analysis of a dried fluid spot on a support by MALDI mass spectrometry overcomes the limitations of the prior art. The present applicant found that the compounds present in a fluid sample may be analyzed easily and rapidly, without any liquid extractions and separation steps, which is advantageous, because the preparation of the sample is faster, and the absence of a liquid extraction step of the compounds present in a dried fluid spot avoid a potential contamination and/or degradation of the compounds. In other words, the method of the invention does not comprise any liquid extraction and separation steps of a compound presents in a dried fluid spot. At least a part of the dried fluid spot on a support is fixed on a conductive surface, without any digestion or liquid extraction step of a dried fluid spot after the deposition of at least one drop of fluid on said support.

In another embodiment, the invention relates to a method for detecting at least one compound present in fluids, wherein a further step of transferring at least one compound present in one dried fluid spot onto a membrane is performed. Accordingly, after providing at least one dried fluid spot on a support, said method comprises the following steps of:
- transferring at least one compound from the dried fluid spot onto a membrane,
- fixing at least a part of said membrane on a conductive surface.

The direct analysis of a dried fluid spot on a support by MALDI mass spectrometry could be challenging for some applications and/or compounds due to the thickness of the original paper support. The proposed indirect approach could overcome this problem by transferring at least one compound onto a thinner support, such as a nitrocellulose or a polyvinylidene fluoride (PVDF) membrane. This embodiment permits to overcome the thickness problem while the spatial localization of the compounds to be analyzed in the dried fluid spot is preserved on the membrane.

In a preferred embodiment, the present invention relates to a method for further determining the spatial distribution of a compound within a dried fluid spot, the method comprising the further steps of:
- acquiring a full scan mode mass spectrum of ions on at least two areas present within a dried fluid spot, a first area being closer to a center of said dried fluid spot area relatively to a second area,
- selecting an accurate mass-to-charge ratio (m/z) corresponding to a calculated mass-to-charge ratio of at least one compound to be detected in the said dried fluid spot area,
- determining a spatial distribution of the compound within the dried fluid spot.

This preferred embodiment allows correlating the presence of a compound with its spatial distribution within the dried fluid spot. This is advantageous, because significant difference of compound localization between central and peripheral areas within a dried fluid spot may impair MS assay results. Compounds distribution studies can be helpful to guide and to optimize local desorption/ionization MS development. Moreover, this preferred embodiment allows correlating the nature, the concentration and the spatial localization of a chosen compound within a dried fluid spot.

Preferably, the compound to be analyzed with the method according to the invention is a compound in fluids with a calculated mass-to-charge ratio comprised between 100 m/z and 1500 m/z.

Indeed, the method according to the invention is particularly relevant when the compound have a mass-to charge ratio comprised between 100 m/z and 1500 m/z. With the method of the invention, these compounds are easily and rapidly identifiable in a dried fluid sample, based on the measured accurate mass-to-charge ratio.

The invention is defined by the independent claims. The dependent claims define advantageous embodiments.

SHORT DESCRIPTION OF THE DRAWINGS

These and further aspects of the invention will be explained in greater detail by way of example and with reference to the accompanying drawings in which:

FIG. 1 shows a schematic representation of direct MALDI mass spectrometry experiment on a dried blood spot according to one aspect of the invention.

Figure 2:
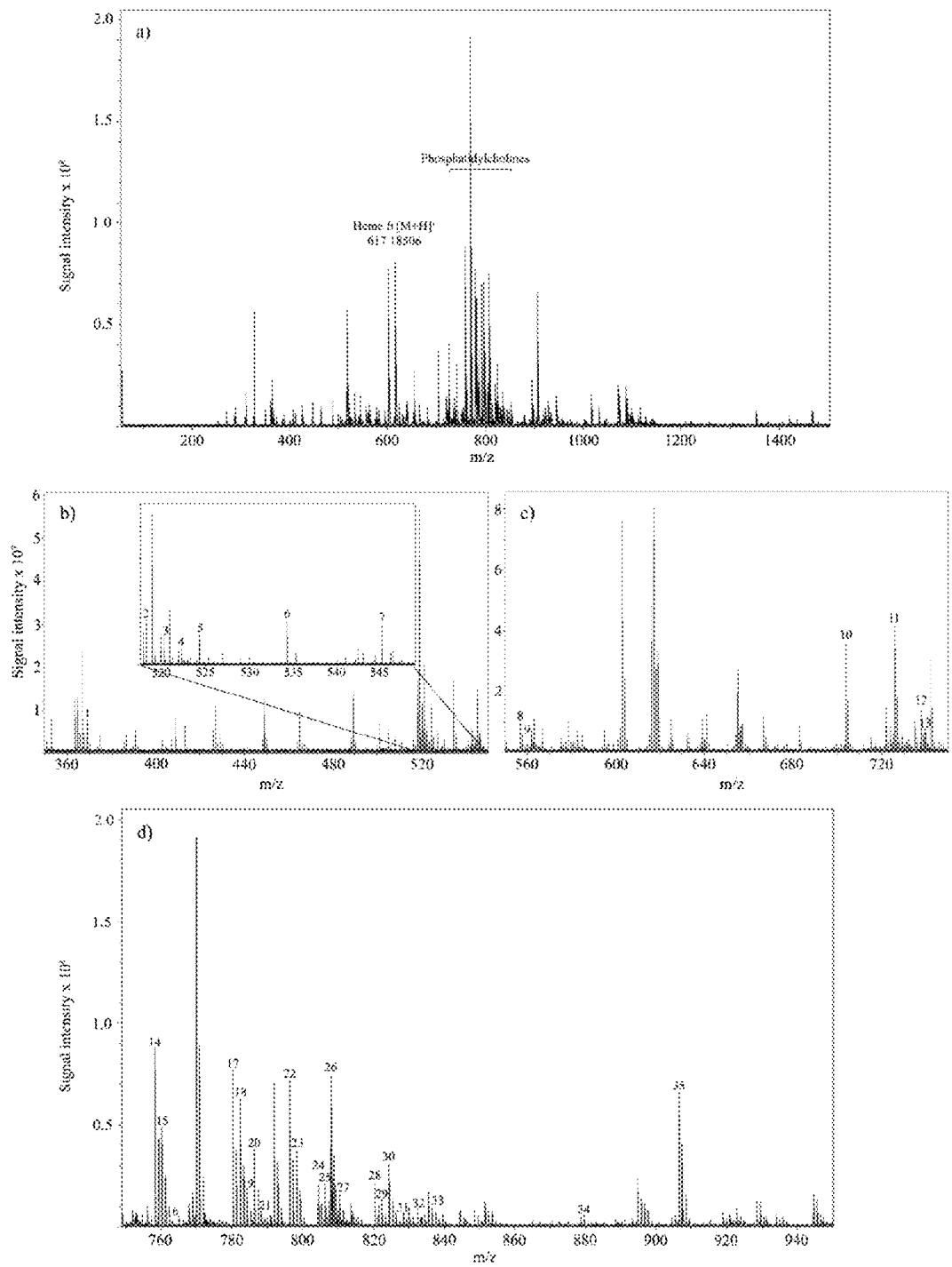

FIG. 2 shows MALDI FT-ICR mass spectra of dried blood spot lipids: (a) Averaged mass spectrum of the 57.75-1500 m/z region; (b) expanded view of the 350-550 m/z region; (c) expended view of the 550-750 m/z region; (d) expended view of the 750-950 m/z region. Mass spectrum annotation (1-35) corresponds to lipid assignment in Table 1.

Figure 3:
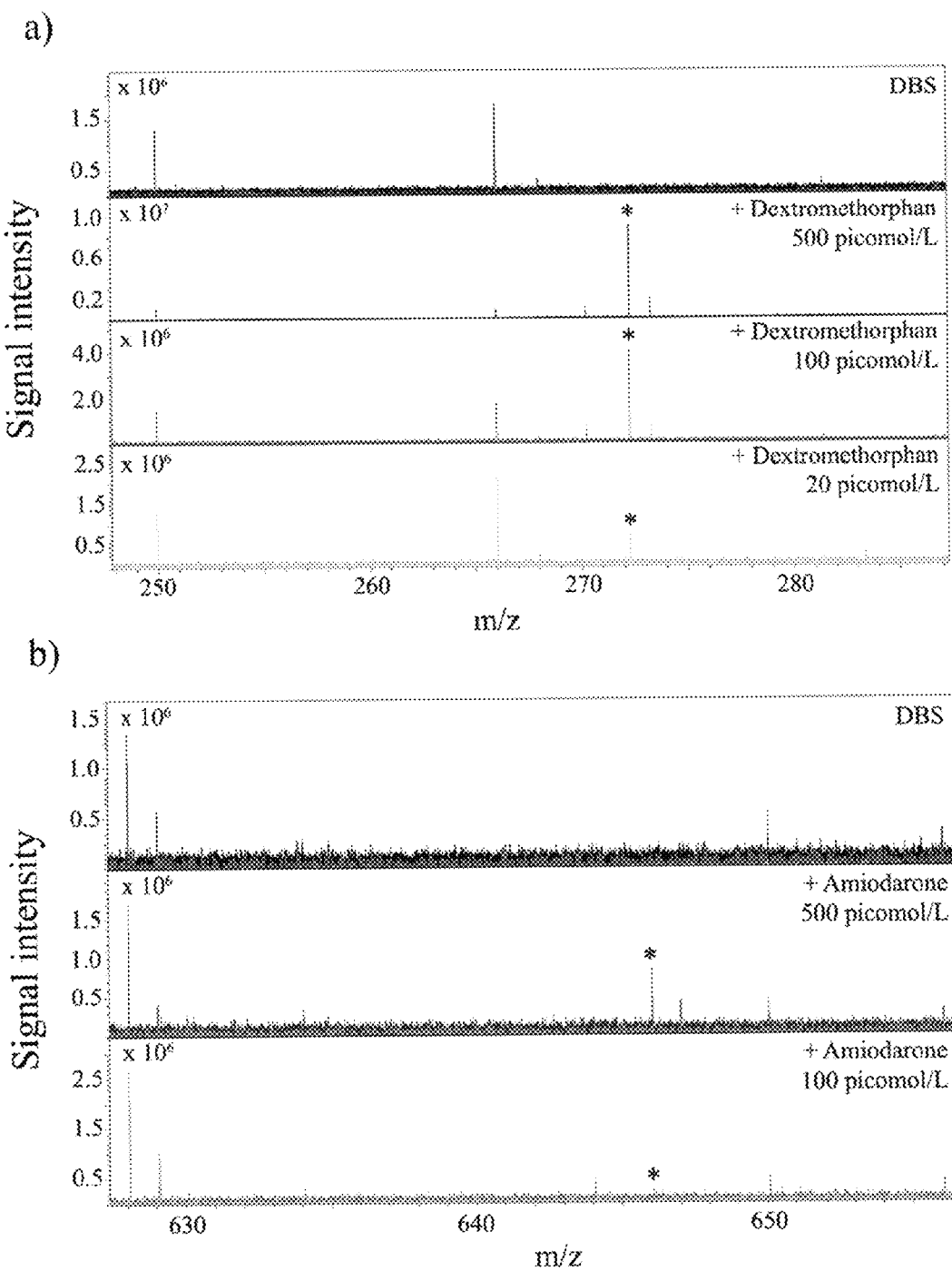

FIG. 3 shows MALDI FT-ICR mass spectra of two small drugs compounds in dried blood spot. (a) Averaged mass spectrum of the 248-287 m/z region showing the [M+H]$^+$ ion of Dextromethorphan (500, 100 and 20 picomol/L); (b) Averaged mass spectrum of the 628-656 m/z region showing the [M+H]$^+$ ion of Amiodarone (500 and 100 picomol/L).

Figure 4:
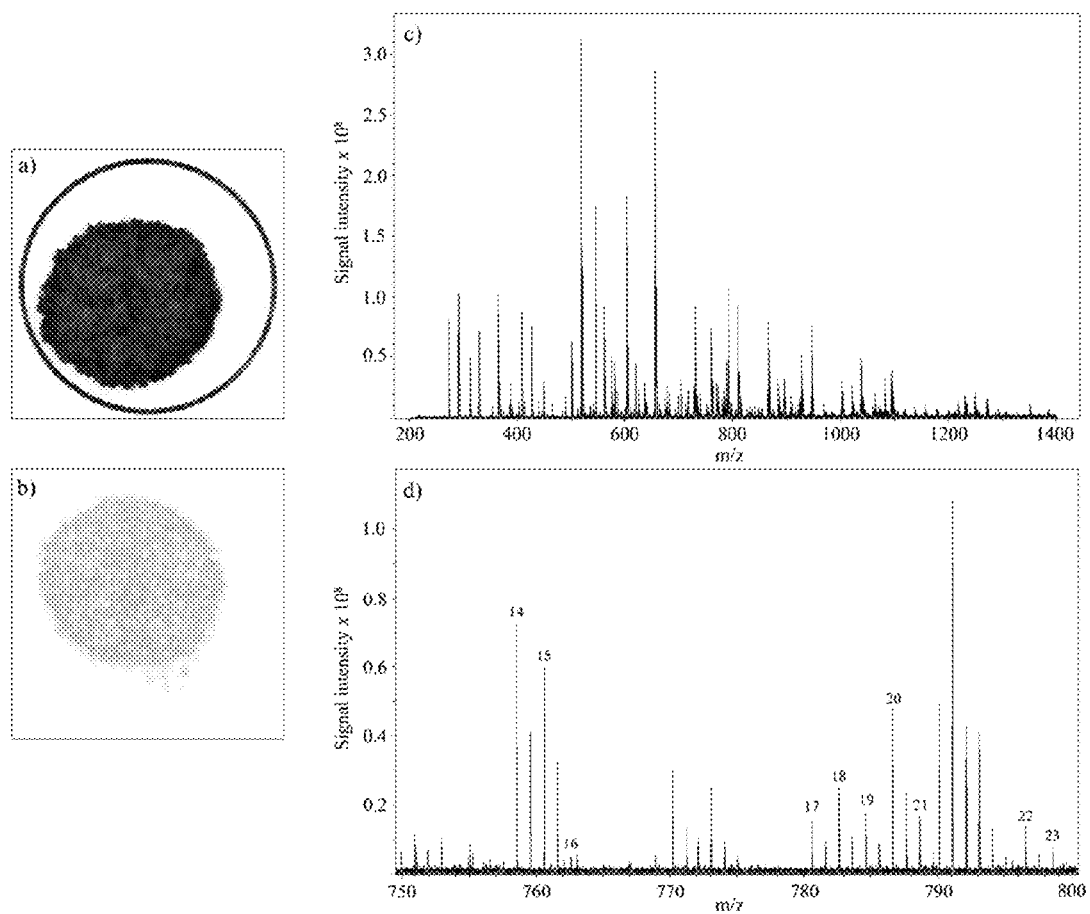

FIG. 4 shows a dried blood spot on a cellulosic support, a transferred PVDF membrane and mass spectrum performed by the method on the membrane. (a) optical image of a dried blood spot; (b) optical image of a transferred membrane stained with Amido black 10B; (c) averaged mass spectrum of the 200-1400 m/z region; (d) expanded view of the 750-800 m/z region. Mass spectrum annotation (14-23) corresponds to lipid assignment in Table 1.

Figure 5:
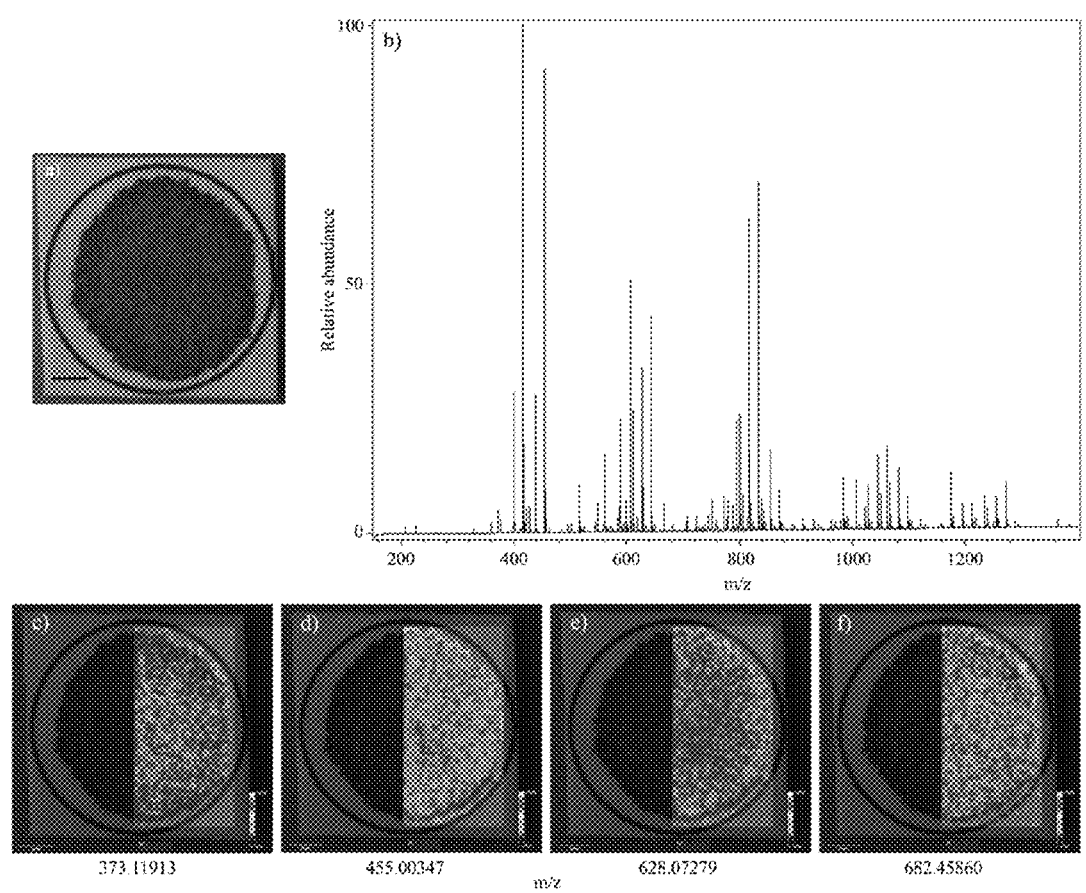

FIG. 5 shows a dried blood spot on a cellulosic support and mass spectrum performed by the method of the invention. (a) optical image of a dried blood spot; (b) averaged MALDI FT-ICR mass spectrum obtained by an analysis of the right half of the dried blood spot; (c) to (f) are ion images of 4 different compounds.

The drawings of the figures are neither drawn to scale nor proportioned. Generally, identical components are denoted by the same reference numerals in the figures.

DETAILED DESCRIPTION OF EMBODIMENTS OF THE INVENTION

By Matrix Assisted Laser Desorption Ionization and Desorption, it is to be understood that MALDI is a soft ionization technique based on the ability of lasers to desorb analyte molecules from surfaces (Laser Desorption Ionization (LDI)-based technique). The use of matrix assists ablation of a sample portion by intense laser pulses over a short duration. The basic of MALDI requires two steps (Hoffmann and Stroobant 2007 [In Mass Spectrometry: Principles and Applications, John Wiley & Sons Ltd]. In the first one, the sample to be analyzed is mixed with a matrix solution and the mixture is dried, resulting in 'analyte-doped matrix crystals'. The second step occurs inside the mass spectrometer source where laser pulses induce heating, sublimation and ablation of the matrix crystals. Analyte molecules are entrained in the matrix plume, ionized and then transferred (intact gas-phase ions) into the mass spectrometer. MALDI source are mainly used in combination with Time-of-Flight mass analyzer (MALDI-TOF) but could be also coupled with Quadrupole-Ion-Trap-TOF (MALDI-QIT-TOF), with Fourier-Transform-Ion-Cyclotron-Resonance (MALDI-FT-ICR), with Linear-Ion-Trap-Orbitrap (MALDI-LTQ-Orbitrap) and with Quadrupole-Orbitrap (MALDI-Q-Orbitrap) mass anlyzers.

Until recently, MALDI was exclusively a vacuum ion source where ions were formed inside the vacuum system of the mass spectrometer (<$10^{-3}$ Torr). With the invention of Atmospheric Pressure MALDI (AP-MALDI), the ionization takes place at normal atmospheric pressure. The ionization process is similar in both sources however they differ by some features. For example, AP-MALDI is a softer ionization technique; ions show less fragmentation at elevated source pressure (up to several torrs). Also, the AP-MALDI source offers the advantage to be external to the mass spectrometer allowing high throughput screening. However AP-MALDI is less sensitive than conventional MALDI. Ions can also be generated at a sub-atmospheric pressure (~3.5 Torr): an intermediate case between conventional MALDI and AP-MALDI. This intermediate pressure method offers a compromise between a good sensitivity (MALDI) and a soft ionization (AP-MALDI).

High mass resolution analyzer, e.g. FT-ICR, allows determination of accurate mass. Mass accuracy is usually expressed in parts per million (ppm) and indicates the deviation of the instrument response from a known monoisotopic mass. FT-ICR instruments provide the highest mass accuracy (<1 ppm). Identification of unknown small compounds in complex samples requires to determine the accurate masses of the compounds. Based on this information, possible (or theoretical) elemental compositions are calculated. Small mass error tolerance helps to reduce the number of candidate formulae, or even to find the correct molecular formula of an unknown compound. The accurate mass term is used to define the experimentally measured mass, while the exact mass defines the true calculated value. In mass spectrometry, the monoisotopic mass is generally used to calculate the exact mass of a compound; it takes into account the exact mass of the most abundant isotope for each constituent element. A mass spectrometer measures a mass-to-charge ratio, m/z.

By biological fluid, it is understood any human or animal body fluid, comprising, but not limited to, blood, serum, plasma, urine, saliva or bile.

By dried fluid spot on a support, it is understood the sampling of biological fluid onto any kind of absorbent cellulosic support. The support could be a specially manufactured paper that is validated in compliance with the requirements of consensus standard (excellent homogenous absorption characteristics). For some applications requiring a biological fluid components separation, the support could also be any chromatographic paper, such as those used for rapid diagnostic tests (strip paper).

By mass spectrum, it is to be understood a spectrum obtained when ions (usually in a beam) are separated according to the mass-to-charge ratios (m/z) of the ionic species present. This plot is a graphical representation of m/z versus measured abundance information (Price 1991 [J Am Soc Mass Spectrom, 2, 336-348]).

By full scan mode, it is to be understood a method describing the operation of a mass spectrometer in which the ion currents are recorded over the entire mass spectrum.

By peak, it is to be understood that a peak represent the signal intensity of an ion detected within a spectrum.

By ionization, it is to be understood a process that produces an ion from a neutral atom or molecule (Price 1991 [J Am Soc Mass Spectrom, 2, 336-348]).

By area, it is to be understood that an area represents a part of a sample to be analyzed (i.e. a dried blood spot), said part being large enough to obtain at least one mass spectrum after a MALDI step. An area may be substantially circular with a diameter comprised between 1 and 15 mm. When at least one compound is transferred from a dried fluid spot onto a membrane, an area refers to the corresponding area of the dried fluid spot that has been transferred onto the membrane.

By mass-to-charge ratio, m/z, it is to be understood the dimensionless quantity formed by dividing the mass of an ion by the number of charges carried by the ion (Price 1991 [J Am Soc Mass Spectrom, 2, 336-348]).

According to a first aspect of the invention, there is provided a method for detecting at least one compound present in fluids, said method comprising the following steps:
 a. providing at least one dried fluid spot on a support,
 b. fixing at least a part of said dried fluid spot on said support on a conductive surface,
 c. providing an aqueous or organic solution of a UV-light-absorbing compound,
 d. depositing said UV-light-absorbing compound on at least a part of said dried fluid spot on said support fixed on said conductive surface,
 e. subjecting at least an area of said dried fluid spot on a support to a Matrix Assisted Laser Desorption Ionization process to produce ions,
 f. acquiring a full scan mode mass spectrum of said ions by a mass analyzer and,
 g. determining the presence of the at least one compound by analysis of the full scan mode mass spectrum.

The fluid sample may be provided from a newborn patient, a child, an adult or an animal. When the fluid sample is blood, it may be collected for example by a puncture in a heel with a sterile blood lancet for example. A fluid drop obtained is deposited onto a support. But alternatively, more than one fluid spot may be deposited onto a support, each one spatially separated from the others. The support may be any kind of support that allows a homogeneous drying of the fluid within the support. For example, the support may be a filter paper, a cellulosic paper, a "Guthrie card" or a Whatman 903 paper. In an alternative embodiment, the fluid has to saturate both sides of the support. In another alternative embodiment, the support may be any kind of chromatographic paper that allows fluid components separation. For example, the support may be a chromatographic paper strip used for rapid diagnostic test. The fluid spot deposited is then air-dried for typically at least two hours at room temperature. The support may then be stored in a sealed envelopes, or containers that will provide protection from contaminants. The dried fluid spot may be stored for a period of at least several weeks to months at a temperature comprised between -20° C. and 23° C., depending on the nature of the compound to be analyzed. In a preferred embodiment, the dried fluid spot is a dried blood spot.

In an alternative embodiment, the step of providing at least one dried fluid spot on a support comprises the steps of:
 providing a liquid fluid sample,
 depositing at least one fluid drop of said liquid sample on at least one support to form at least one dried fluid spot on a support.

The surface of the dried fluid spot on the support may have a diameter comprised between less than few to a dozen millimeter. For example, the diameter of the dried fluid spot may be ranging between 5 and 20 mm when a single drop is deposited. Such dried fluid spot diameter is obtained with any cellulose matrix provided that it has a homogenous composition and uniform thickness, flow-rate and absorbency, such as those commercially available (Whatman 903 cards or Whatman FTA DMPK cards for example). In another embodiment, the surface of the dried fluid spot on the support may have a size of few millimeters in width and few centimeters in length. Such dried fluid spot size is obtained with any chromatographic cellulose support after a chromatographic separation step.

At least a part of a dried fluid spot on a support or a part of the blotted membrane is then fixed on a conductive surface. For example, only a part of the dried fluid spot on a support or of the blotted membrane may be cut out the support and then fixed on a conductive surface. For example, at least 10%, 20%, 30%, 40%, 50%, 60%, 70%, 80% or 90% of the surface of the dried fluid spot on a support may be cut out of the support and then fixed on a conductive surface. For example, a punch hole sample of the supports may be directly spotted on a conductive surface. In a preferred embodiment, when at least a part of a dried fluid spot is fixed on a conductive surface, the fixed part comprises at least a center area and a peripheral area of the dried fluid spot (a dried fluid spot being generally substantially a disc, it means that the fixed part comprises a circular sector delimited by 2 radius and the perimeter of the dried fluid spot). With such configuration, it is possible to analyze areas that are more or less peripheral within a dried fluid spot.

In an alternative embodiment, at least one compound present in one dried fluid spot may be transferred onto a membrane before fixation on a conductive surface. In the said method, after providing at least one dried fluid spot on a support, the step (b) of the method consists of:
transferring at least one compound from the dried fluid spot onto a membrane,
fixing at least a part of said membrane on a conductive surface, The technique is based on a pressure blotting method to transfer compound from a dried fluid spot to the surface of a membrane. A membrane may be defined as any immobilizing support material suitable for further analyzing biological compounds blotted onto it. A membrane could be, but is not limited to, a nitrocellulose, a polyvinylidine difluoride (PVDF), a polyethylene or a nylon support. Blotting could be assisted by pre-wetting the membrane with a solvent such as, but not limited to, acetone, ethanol, methanol, propanol or a mix thereof. Also, blotting could be assisted by heat. Blotting could be done manually or with a (thermal) blotter.

The part of the dried fluid spot on a support or the part of the blotted membrane may be fixed onto a conductive surface by using a double-sided conductive adhesive tape, for example a double-sided conductive carbon tape. Conductive surface provides an electrically conductive planar surface to enhance the ionization process and to avoid electrostatic charges affecting ion plume formation. Conductive surface may include plastics, glass and metal; the surface may be rendered conductive in a variety of ways such as, but not limited to, carbon particles, carbon fibers and metal particles. For example, a conductive surface may be selected within the group comprising but not limited to, an Indium Tin Oxide (ITO) coated glass side, a stainless steel plate or a gold-coated plate, with common size range from 25 mm×75 mm (glass side) to 81 mm×123 mm (plate).

An UV-light-absorbing compound refers to a material used in MALDI-MS to prepare a sample for analysis (also known as a matrix, or a matrix solution). This material is at least one UV-light-absorbing compound dissolved in an organic solvent and/or water. An aqueous or organic solution of a UV-light-absorbing compound deposited on a sample absorbs energy from a laser and transfers it to the sample to desorb, volatize, and ionize a compound presents in the dried fluid spot on a support, thereby producing ions from the sample that are then analyzed in a mass spectrometer to yield information about a compound presents in a dried fluid spot. In other words, a UV-light-absorbing compound may be any compound that permits the further ionization, volatilization and desorption of at least one compound comprised in a dried fluid spot on a support (or of at least one compound blotted on a membrane) by a MALDI method.

The UV-light-absorbing compound is dissolved in water, or in at least one organic solvent, or a mixture of water and at least one organic solvent and water. For example, the organic solvent may be, but not limited to, acetone, acetonitrile, chloroform, ethanol, isopropanol, methanol, tetrahydrofuran and a mixture of solvents. A typical matrix solution would comprise the matrix at a concentration of 5-30 mg/ml in a solvent that is compatible with the target compounds to be analyzed. In a preferred embodiment, matrix additives such as ammonium citrate, fucose, spermine or spermidine may be used to suppress undesirable cationization.

In a preferred embodiment an acid may be added to the dissolved UV-absorbing compound in order to enhance the ionization. For example, acid may be formic acid, trifluoroacetic acid or phosphoric acid preferably at 0.05-1% v/v, acetic acid or chlorhydric acid preferably at a concentration ranging from 0.01-0.2 mol/L.

At least one dissolved UV-light-absorbing compound is deposited on at least a part of the support comprising a dried fluid spot or a blotted membrane fixed on a conductive surface. The deposition of the dissolved UV-light-absorbing compound may be performed by vaporization of the UV-light-absorbing compound with a manual airbrush, with an automatic sprayer (e.g. an automated spray nozzle or a piezoelectric nebulizer), a pneumatic sprayer or a mix thereof. After deposition of the dissolved UV-light-absorbing compound, a mixture comprising compounds present in a dried fluid spot or a blotted membrane and the dissolved UV-light matrix is formed.

In a preferred embodiment, the dissolved UV-light-absorbing compound is deposited as a homogenous layer on the support comprising a dried fluid sample or a blotted membrane. At least a part of the mixture made of compounds in the dried fluid spot or the blotted membrane and the UV-light-matrix is desorbed and ionized by MALDI. The UV-light-absorbing compound absorbs energy from the laser and transfers the energy to the compounds to be desorbed in the dried fluid spot, allowing their volatization and ionization, thereby producing ions that are then analyzed.

The last step of the detection and/or identification of a compound is performed by acquiring a full scan mode mass spectrum of ions of dried fluid spot compounds by a mass spectrometer analyzer. The full scan mode mass spectrum may be an average of several full scan mode mass spectra acquired at different positions of the dried fluid spot area or the blotted membrane area.

Data acquisition is controlled by a mass spectrometer acquisition software after setting the mode (positive or negative), the mass range, the laser intensity and frequency, the number of shots per spectrum and any other parameters of the mass spectrometer, according to the manufacturer's specific recommendations. Data analysis is then performed with a mass spectrometer analysis software; the mass spectra are smoothed, the baseline is subtracted and peaks on the mass spectrum are manually or automatically picked. For imaging, an optical image is first recorded. Data acquisition and analysis are controlled by a specific MS imaging software; an ion density map may be created for each signal present on the whole sample average mass spectrum.

In a preferred embodiment, the determination of the presence of at least one compound present in fluids is performed by selecting at least one accurate mass-to-charge ratio (m/z)

ions corresponding to at least one calculated mass-to-charge ratio (m/z) of at least one compound present in the said dried fluid spot. With such step, the presence of a single or a multiplicity of known compounds may be analyzed within a single mass spectrum. An operator skilled in the art may found exact mass of known compounds in reference molecular tables or in web-based databases well known in the art.

In a preferred embodiment, the last step of the analysis, i.e. mass spectra acquisition of ions, is performed by a Fourier-Transform—Ion-Cyclotron-Resonance mass analyzer (FT-ICR-MS), a Time-of-Flight mass analyzer (TOF-MS), a Quadrupole-Ion-Trap-Time-of-Flight mass analyzer (QIT-TOF-MS), a Quadrupole-Orbitrap mass analyzer (Q-Orbitrap MS) or a Linear-Ion-Trap-Orbitrap mass analyzer (LTQ-Orbitrap MS). In a more preferred embodiment, a FT-MS instrument (ICR or Orbitrap) is used. A FT-MS provides a high resolution, a large mass range, high sensitivity and accurate mass for determining the identity of small molecules.

In a more preferred embodiment, the compound to be detected is a compound that has a calculated mass-to-charge ratio lower than or equal to 15000 m/z, preferably comprised between 100 m/z and 1500 m/z. When a compound has a calculated mass-to-charge ratio lower than or equal to 1500 m/z, identification by accurate mass is possible provided that accuracy of the mass spectrometer is sufficient (<1 ppm).

In a preferred embodiment, the compound to be detected is selected within the group comprising nucleotides, amino acids, organic acids, carbohydrates, lipids, urea, myo-inositol, said compounds being present in the body metabolome, drug candidates and pharmaceutical candidates. In a more preferred embodiment, the compound to be detected is a compound from the a selected fluid metabolome (urine metabolome, plasma metabolome, blood metabolome, serum metabolome, saliva metabolome, bile metabolome), and in a more preferred embodiment the compound to be detected is a compound from the blood metabolome. The metabolome may be defined as the complete set of small-molecule metabolites to be found within a biological sample. The body fluid metabolome may comprise endogenous compounds and exogenous compounds. For example, an endogenous compound to be analyzed and/or identified may be selected within the group comprising: nucleotides (e.g. Mono-, Di- and Triphosphate ribonucleotides : Adenosine monophosphate, Adenosine triphosphate, Adenosine triphosphate, Uridine diphsophate), amino acids (e.g.L-Proline, L-Phenylalanine, L-Methionine, L-Threonine, L-Tryptophan L-Glutamine), organic acids (e.g. Benzoic acid, Fumaric acid, Tartaric acid, Citric acid, Malonic acid, Uric acid, Succinic acid), carbohydrates (e.g. D-Fructose, D-Galactose, D-Glucose, D-glucopyranose, N-acetyl-D-glucosamine), lipids (e.g. cholesterol, free fatty acids, glycerophospholipids, sphingolipids, steroids, glycolipids, diacylglycerols and triacylglycerols), urea, or myo-inositol. For example, an exogenous compound to be analyzed and/or identified may be selected within the group comprising drug candidates (during preclinical studies of a drug for example), pharmaceutical molecules (during a clinical study or a therapeutic drug monitoring), like Dextromethorphan or Amiodarone.

FIG. 2 shows an example of a lipid profile obtained by the method of the present invention on a dried blood spot in positive ion mode. Heme b and phosphatidylcholines species dominate the average mass spectrum. Table 1 lists non exhaustively the different classes of lipids detected in the sample. Table 1 represents assignments of the peaks detected in the mass spectra recorded in the positive-ion mode of a dried blood spot. Assignments have been made on the basis of the comparison with the literature data. The used abbreviations are: CH, cholesterol; LPC, lysophosphatidylcholine; PC, phosphatidylcholine; PE, phosphatidylethanolamine; PI, phosphatidylinositol; PS, phosphatidylserine; SM, sphingomyelin; TAG, triacylglycerol.

TABLE 1

Non-exhaustive list of compounds detected in an area of a dried blood spot.

| | Molecular species | m/z measured |
|---|---|---|
| 1 | CH $-H_2O$ $+H^+$ | 369.34801 |
| 2 | LPC16:0 $+Na^+$ | 518.32653 |
| 3 | LPC18:2 $+H^+$ | 520.33404 |
| 4 | LPC18:1 $+H^+$ | 522.36076 |
| 5 | LPC18:0 $+H^+$ | 524.36347 |
| 6 | PC 16:0/16:0 $+H^+$ | 534.30498 |
| 7 | LPC18:0 $+Na^+$ | 546.35966 |
| 8 | PC16:0/16:0 $+Na^+$ | 557.15604 |
| 9 | LPC19:0 $+Na^+$ | 560.31139 |
| 10 | SM16:0 $+H^+$ | 703.57955 |
| 11 | SM16:0 $+Na^+$ | 725.55982 |
| 12 | PE16:0/18:2 $+Na^+$ | 738.45646 |
| 13 | PE16:0/18:1 $+Na^+$ | 740.48319 |
| 14 | PC16:0/18:2 $+H^+$ | 758.57001 |
| 15 | PC16:0/18:1 $+H^+$ | 760.59193 |
| 16 | PE16:0/18:1 $-H^+$ $+2Na^+$ | 762.58503 |
| 17 | PC16:0/18:2 $+Na^+$ − SM20:0 $+Na^+$ | 780.55659 |
| 18 | PC16:0/20:4 $+H^+$ − PC16:0/18:1 $+Na^+$ | 782.56410 |
| 19 | PS16:0/18:1 $+H^+$ $+Na^+$ − PC18:0/18:3 $+H^+$ | 784.58121 |
| 20 | PC18:0/18:2 $+H^+$ | 786.59353 |
| 21 | PC18:1/20:4 $+H^+$ − PC18:0/18:2 $+Na^+$ | 788.61065 |
| 22 | PC16:0/18:2 $+K^+$ | 796.53504 |
| 23 | PC16:0/18:1 $+K^+$ | 798.54255 |
| 24 | PC16:0/20:4 $+Na^+$ | 804.55068 |
| 25 | PS16:0/18:1 $+2Na^+$ − PC16:0/22:6 $+H^+$ − PC 18:0/18:3 $+Na^+$ | 806.57260 |
| 26 | PC18:0/18:2 $+Na^+$ − PC 18:1/20:4 $+H^+$ | 808.58011 |
| 27 | PC18:0/20:4 $+H^+$ − PC 18:0/18:1 $+Na^+$ | 810.60683 |
| 28 | PC18:1/18:3 $+K^+$ − PC 16:0/20:4 $+K^+$ | 820.52432 |
| 29 | PC18:1/18:2 $+K^+$ | 822.54624 |
| 30 | PC18:0/18:2 $+K^+$ | 824.56336 |
| 31 | PC16:0/22:6 $+Na^+$ | 828.54477 |
| 32 | PC18:0/20:4 $+Na^+$ | 832.57900 |
| 33 | SM24:0 $+Na^+$ | 837.67943 |
| 34 | PI16:0/18:2 $-H^+$ $+2Na^+$ | 879.58264 |
| 35 | TAG C18/18/18:2 | 906.21124 |
| | Heme b | 617.18506 |

As we can see, phospholipids (lysophosphatidilcholine, phosphatidylcholine, phosphatidylethanolamine, phosphatidylinositol, phosphatidylserine), sphingolipids (sphingomyelin), triacylglycerol and cholesterol are the major species observed. Plasma lipids have been shown to be potential biomarkers for several diseases such as rheumatoid arthritis (Fuchs et al., 2005 [Clinical Biochemistry 38, 925-933] or cardiovascular disease (Stubiger et al., 2012 [Atherosclerosis 224, 177-186]. The present invention represents a promising technique for clinical screening of lipid profile in dried blood spot to evaluate disease state and/or disease activity before or after treatment.

FIG. 3 shows the average spectrum of two small drug molecules. Dextromethorphan is an antitussive drug ($C_{18}H_{25}NO_3$, monoisotopic neutral mass 271.19361) and Amiodarone ($C_{25}H_{29}I_2NO_3$, monoisotopic neutral mass 645.02368) is an antiarrhythmic agent used for various types of cardiac dysrhythmias. Dextromethorphan [M+H$^+$] ion (measured mass 272.20012 m/z) and Amiodarone [M+H$^+$] ion (measured mass 646.03071 m/z) are designated with an asterisk.

FIG. 4 shows a dried blood spot (FIG. 4a) from which compounds have been transferred onto a PVDF membrane (FIG. 4b). The PVDF membrane has been pre-wetted in MeOH for 10 seconds and then applied onto the dried blood spot for 2 minutes; compounds are transferred at 180° C. with an iron. The membrane is stained with Amido black 10B (0.1% in MeOH:H$_2$O, 45:55) for 30 seconds and rinsed twice in distilled H$_2$O (30 seconds). Amido black 10B is used to stain proteins and/or lipids. The expanded view of the 750-800 m/z region shows some classes of lipids. Mass spectrum annotation (14-23) corresponds to lipid assignments in Table 1.

In a preferred embodiment, a calibration mixture is deposited on a conductive surface where a dried fluid spot on a support or a blotted membrane is fixed; and a UV-light-absorbing compound is deposited on at least a part of the calibration mixture and on at least a part of the dried fluid spot on a support. The UV-light-absorbing compound may be the same as the one deposited on the sample of dried fluid spot. A calibration mixture may be a homemade or a commercially pre-packaged (from Sigma, Bruker, AB Sciex for example) compounds mixture with known mass-to-charge ratios. The calibration mixture is used to calibrate the MS device. The calibration mixture is chosen in relation with the nature of the compound to be analyzed and/or identified. For example, when the compound to be identified and/or analyzed has a calculated mass-to-charge ratio comprised between 100 m/z and 1500 m/z, the calibration mixture comprises or consists of compounds with a calculated mass-to-charge ratio comprised between 100 m/z and to 1500 m/z. Standard small molecules, peptides or a mixture of both may be used.

With this embodiment, the result of the method is greatly improved because the sample to be analyzed and the calibration mixture are prepared in the same conditions. Because the samples analysis is greatly dependent on the accuracy of the measurement, by having a known calibration mixture prepared in the same way than the sample permits to calibrate reliably the m/z scale of the mass analyzer.

Accordingly, in a more preferred embodiment, the method comprises the following steps:
subjecting at least an area of the calibration mixture to a Matrix Assisted Laser Desorption Ionization to produce calibration ions,
acquiring a full scan mode mass spectrum of calibration ions by a mass analyzer,
using the mass spectrum of said calibration ions to calibrate the m/z scale of the mass spectrometer,
wherein the two first steps are performed before or after the step of subjecting at least an area of a dried fluid spot on a support or a blotted membrane to MALDI to produce ions.

In other words, a step of desorption/ionization and a step of acquiring mass spectra of calibration ions corresponding to compounds present in the calibration mixture are performed before or after the similar step performed on the support comprising the dried fluid spot and UV-light-absorbing compound mixture. In this embodiment, the MALDI device and/or the MS device is calibrated by an external calibration method and the analysis of the compound present in a dried fluid spot is greatly improved.

In a preferred embodiment, calibration could be also made using internal molecules of known mass-to-charge ratios, present in large amount in fluids, such as heme b molecule (C$_{34}$H$_{32}$FeN$_4$O$_4$, monoisotopic neutral mass 616.177298) in blood. This correction is done post data acquisition by an internal calibration method provided by the mass spectrometer data analysis software.

In a more preferred embodiment of the present method, the UV-light-absorbing compound is a crystalline matrix selected within the group comprising alpha-cyano-4-hydroxycinnamic acid (CHCA); dihydroxybenzoic acid (DHB) isomers; trans-3,5-dimethoxy-4-hydroxycinnamic acid (SA); nicotinic acid; picolinic acid (PA); trans-3-methoxy-4-hydroxycinnamic acid (ferulic acid); 2,4,6-trihydroxyacetophenone (THAP); 2,6-dihydroxyacetophenone (DHA); 3-hydroxypicolinic acid (HPA); 3-aminoquinoline; trans-3-indoleacrylic acid (IAA); dithranol (DIT); 1,8,9-trihydroxyanthracene; 2-(4-hydroxyphenylazo)-benzoic acid (HABA); 6-aza-2-thiothymine (ATT); 3-amino-4-methyl-5-nitropyridine (AMNP); 5-amino-l-naphthol (5,1-ANL); 5-hydroxy-l-naphthol (5,1-HNL); or a mix thereof.

The UV-light-absorbing compounds may also be comprised in solid ionic matrices, obtained from the mixture of acidic crystalline matrices such as CHCA, SA or DHB with different bases like aniline or N,N-dimethylalinine or in liquid ionic matrices, such as CHCA/2-amino-4-methyl-5-nitropyridine; 4-Nitrobenzylalcohol (NBA). Porphyrin-based matrix (e.g. 10,15,20-tetrakis(pentafluorophenyl)porphyrin, F20TTP) or inorganic matrices (fine metal or a metal oxide in glycerol suspensions), could also be used.

In a more preferred embodiment, the invention further provides a method for determining the spatial distribution of at least one compound into a dried fluid spot or into a blotted membrane wherein the said method comprises the further steps of:
acquiring a full scan mode mass spectrum of ions on at least two areas present within a dried fluid spot, a first area being closer to the center of said dried fluid spot relatively to a second area,
selecting an accurate mass-to-charge ratio (m/z) ions corresponding to a calculated mass-to-charge ratio of at least one compound to be detected in the said dried fluid spot,
determining a spatial distribution of at least one compound within the dried fluid spot.

In this embodiment, it is possible to determine the spatial localization of at least one compound within a dried fluid spot or onto a blotted membrane. The MALDI MS generates mass spectra of ions from a compound present in a dried fluid spot on a support that may be correlated to a spatial distribution of a compound within the support.

The physical localization of a compound, or compounds, may be of significant relevance when analyses are performed by direct desorption. It has been shown that the chromatographic migration of compounds present in blood when blood is sampled on a cellulosic support may be linked to several factors (hematocrit level, blood spot volume or diffusion properties). Hence, there is a need for a fast method, with few steps that permits a spatial distribution analysis of at least one compound present in a dried fluid spot on a support or into a blotted membrane. A localization step by imaging in the dried fluid sample on a support or into a blotted membrane is proposed in the current invention to direct detection analyses. Hence, both detection and visualization of a compound, or compounds, are easily made by this single method approach without any compound preselection. When a fluid sample is deposited onto a chromatographic paper, and a step of separation of the fluid sample on the chromatographic paper is performed, analyzes may be performed onto a limited part of the dried fluid sample (for example onto part limited to a specific range of molecular weight). In this case, a center area is an area located on the center of the chromatographic paper, and a second area being closer to the edge of the chromatographic paper.

Spatial distribution of compounds may be recorded by FT-ICR MS imaging within a dried fluid spot on a cellulosic support. An example of such imaging may be seen on FIG. 5(c) to FIG. 5(f). A solution of CHCA matrix (5 mg/ml) in acetone/water (0.1% TFA) 7:3 v/v was applied by sparying (ImagePrep, Bruker Daltonic). The FT-ICR, SolariX, equipped with a 9.4 Tesla magnet (Bruker Daltonics), was operated in positive-ion mode. As we can see, the spatial distributions of 4 different compounds are shown: (c) the compound of interest is distributed exclusively in the central zone; (d) the compound of interest is distributed more in the peripheral zone; (e) the compound of interest is distributed exclusively in the peripheral zone; (f) the compound of interest is distributed homogeneously (f).

For imaging, an optical image is first recorded. Data acquisition and analysis are controlled by specific MS imaging software; an ion density map is created for each signal present in the whole sample average mass spectrum. With the method of the invention, it is possible to achieve a 5 µm spatial resolution by using an atmospheric pressure scanning microprobe MALDI imaging source (AP-SMALDI) and by using a matrix application method with a pneumatic sprayer. Imaging is thus performed by combining accurate mass analysis and a higher spatial resolution at the same time.

In a more preferred embodiment or in an alternative embodiment, the invention provides a method wherein the said method is performed on at least two different dried fluid spots. The at least two different dried fluid spots may be dried fluid spots collected from a single fluid sample from a single person or animal, or collected from fluid samples collected at different times from a single person or animal (i.e. before and after a treatment), or collected from two different persons or animals in order to compare the analysis and/or identification of a compound in both persons or both animals. With this method, it is possible to determine the spatial distribution of at least one compound within a plurality of dried fluid spot on a plurality of supports or within a plurality of blotted membranes from a plurality of dried fluid spots.

Accordingly, in a more preferred embodiment, the method comprises the provision of at least two dried fluid spots, wherein the step of acquiring a full scan mode mass spectrum of the method is realized on at least two areas of each different dried fluid spots provided, said method also comprising the step of:
- comparing the spatial distribution of the at least one compound to be detected between the different dried fluid spots provided.

EXAMPLES

Detection of Lipids from a Dried Blood Spot Sample on a Cellulosic Support (Table 1, FIG. 2).

A blood spot from a human subject was provided and deposited on a cellulosic support (Whatman 903).

A sample of the dried blood spot on the cellulosic support is cut off from the cellulosic support and fixed on a conductive ITO-coated glass slide (Bruker Daltonics) by using a double-sided conductive adhesive carbon tape (SPI supplies). A calibration mixture (Peptide Calibration Standard II, Bruker Daltonics) is deposited close to sample of the dried blood spot on a cellulosic support and is air dried.

The UV-light-absorbing compound is the 2,5-DHB. The DHB is dissolved at a concentration of 20 mg/ml in methanol/0.2% TFA (50:50 vol/vol). The dissolved DHB is sprayed with an ImagePrep device (Bruker Daltonics).

The spraying process is a multi-steps process: the first step comprises 12 cycles of spray of dissolved DHB at a spray power of 25±30% (scale from 0 to 100% of the maximum available spray power with its power modulation which means in this case that the spray power varied from 0 to 55%) followed by a drying time of 50 seconds between each spray cycle. This step is followed by a drying step of 30 s. Then, three subsequent steps were applied at a spray power of 25±30%, with increasing cycle numbers of spray (step 2: between 8 and 12 cycles, step 3: between 16 and 32 cycles and step 4: between 36 to 60 cycles). The number of cycles between each complete drying phase was also increasing (every two cycles for step 2, every four cycles for step 3 and every 6 cycles for step 4).

After deposition of the UV-light-absorbing compound and its drying, the ITO-coated glass slide is loaded into a MALDI-FT-ICR apparatus (SolariX 9.4 T, Bruker Daltonics). The sample is ionized in positive mode with a laser power of 25% and with a laser frequency of 1000 Hz. The mass range was set between 57.75 and 1500 m/z. The quadripole 1 mass was set on 650 m/z and an average of 30 mass spectra were accumulated. The external calibration resulted in a mass accuracy of <0.15 ppm under these conditions. Two dimers ($[2DHB-2H_2O+H]^+$ and $[2DHB-H_2O+Na]^+$) and two trimers ($[3DHB-3H_2O+H]^+$ and $[3DHB-2H_2O+Na]^+$) of DHB as well as the heme b and the bradykinin 1-7 peptide (Peptide Calibration Standard II, Bruker Daltonics) were used as external calibrators. Mass spectra were analyzed with DataAnalysis 4.0. Peaks originating from matrix or the cellulosic support were subtracted from the average mass spectrum. Lipid peaks assignment has been made on the basis of the comparison with the literature data.

With the method of the invention, at least 35 lipids present in a blood metabolome were identified.

Detection of Exogenous Small Drug Compounds from Dried Blood Spot Sample on a Cellulosic Supports (FIG. 3).

Stock solutions (1 mmol/L) of Dextromethorphan and Amiodarone were prepared in $H_2O$ and $H_2O$-methanol (1:1, v/v), respectively. Working solutions were prepared by diluting the stock solutions at concentration of 500, 100 and 20 pmol/L with blank whole human blood. Aliquots of blood working solutions (25 pl) were spotted onto Whatman 903 cellulosic paper with a pipet and allowed to dry at room temperature for 3 hours. Dried blood spot samples were then stored at -20° C. in a sealed plastic bag containing desiccant until analysis.

Sample of dried blood spots on the cellulosic support were cut off from the cellulosic support and fixed on a conductive ITO-coated glass slide (Bruker Daltonics) by using a double-sided conductive adhesive carbon tape (SPI supplies).

The UV-light-absorbing compound was CHCA. CHCA was dissolved at a concentration of 5 mg/ml in acetonitrile/ 0.2% TFA (70:30 vol/vol). The dissolved CHCA was sprayed with an ImagePrep device (Bruker Daltonics).

The spraying process is a multi-steps process: the first step comprises 12 cycles of spraying of dissolved DHB at a spray power of 20±20% (scale from 0 to 100% of the maximum available spray power with its power modulation which means in this case that the spray power varied from 0 to 55%) followed by a drying time of 20 seconds between each spray cycle. Then, three subsequent steps were applied at a spray power of 22±22%, 19±19% and 20±20%, respectively, with increasing cycle numbers of spraying (step 2: between 6 and 18 cycles, step 3: between 12 and 40 cycles and step 4: between 30 to 60 cycles). The number of cycles between each complete drying phase was also increasing (every two cycles for step 2, every four cycles for step 3 and every 6 cycles for step 4).

After deposition of the UV-light-absorbing compound and its drying, the ITO-coated glass slide was loaded into a MALDI-FT-ICR apparatus (SolariX 9.4 T, Bruker Daltonics). The sample was ionized in positive mode with a laser power of 50% and with a laser frequency of 1000 Hz. The mass range was set between 200 and 800 m/z. The quadripole 1 mass was set on 300 m/z and an average of 15 spectra were accumulated. The external calibration resulted in a mass accuracy of <1 ppm under these conditions. One monomer ([CHCA+Na]$^+$), three dimers ([2CHCA-H$_2$O+H]$^+$, [2CHCA+H]$^+$ and [2CHCA+Na]$^+$) and one trimer ([3CHCA+Na]$^+$) of CHCA were used as external calibrators. Mass spectra were analyzed with DataAnalysis 4.0. As we can see, detection of small drug compounds was performed on a dried blood spot accordingly to the method of the invention, leading to a fast and reliable analysis of the presence of a drug compound.

The present invention has been described in terms of specific embodiments, which are illustrative of the invention and not to be construed as limiting. More generally, it will be appreciated by persons skilled in the art that the present invention is not limited by what has been particularly shown and/or described hereinabove.

Reference numerals in the claims do not limit their protective scope.

Use of the verbs "to comprise", "to include", "to be composed of", or any other variant, as well as their respective conjugations, does not exclude the presence of elements other than those stated.

Use of the article "a", "an" or "the" preceding an element does not exclude the presence of a plurality of such elements.

The invention may also be described as follows: It is provided a method for detection and/or quantification of at least one molecule presents in biological fluids by a MALDI-MS analysis of a dried fluid spot without the presence of any digestion step or liquid extraction step, which permits to further analyse the physical distribution of at least one molecule within a dried fluid spot.

The invention claimed is:

1. A method for detecting at least one compound present in fluids, said method comprising the following steps:
    a. providing at least one dried fluid spot on a support,
    b. fixing at least a part of said dried fluid spot on said support on a conductive surface,
    c. providing an aqueous or organic solution of a UV-light-absorbing compound,
    d. depositing said UV-light-absorbing compound on at least a part of said dried fluid spot on said support fixed on said conductive surface,
    e. subjecting at least an area of said dried fluid spot on said support to a Matrix Assisted Laser Desorption Ionization process to produce ions,
    f. acquiring a full scan mode mass spectrum of said ions by a mass analyzer and,
    g. determining a presence of the at least one compound by analyzing the full scan mode mass spectrum.

2. The method according to claim 1, wherein the step (b) consists of:
    transferring at least one compound from the dried fluid spot onto a membrane,
    fixing at least a part of said membrane on a conductive surface.

3. The method according to claim 1, wherein the step of providing a dried fluid spot on a support comprises the steps of:
    providing a biological fluid sample,
    depositing at least one fluid drop of said fluid sample on at least one support to form at least one dried fluid spot on a support.

4. The method according to claim 1, wherein the step (g) is performed by selecting at least one mass-to-charge ratio (m/z) ions corresponding to an at least one calculated mass-to-charge ratio (m/z) of at least one compound present in the said dried fluid spot area.

5. The method according to claim 1, wherein the step of acquiring a full scan mode mass spectrum of said ions is performed by a Fourier-Transform-Ion-Cyclotron-Resonance mass analyzer, a Time-of-Flight mass analyzer, a Quadrupole-Ion-Trap-Time-of-Flight mass analyzer, a Quadrupole-Orbitrap mass analyzer, or Linear-Ion-Trap-Orbitrap mass analyzer.

6. The method according to claim 1, wherein the compound to be detected is a compound with a calculated mass-to-charge ratio lower than or equal to 1500 m/z.

7. The method according to claim 1, wherein a calibration mixture is additionally deposited on said conductive surface and wherein the UV-light-absorbing compound is deposited on at least a part of said calibration mixture prior to step (e).

8. The method according to claim 7 further comprising the steps of:
    h. subjecting at least an area of the calibration mixture to a Matrix Assisted Laser Desorption Ionization process to produce calibration ions,
    i. acquiring a full scan mode mass spectrum of said calibration ions by a mass analyzer,
    j. using the mass spectrum of said calibration ions to calibrate a m/z scale of the mass analyzer,
        wherein the steps (i) to (j) are performed before or after the step (e).

9. The method according to claim 1, wherein the UV-light-absorbing compound is selected from the group consisting of alpha-cyano-4-hydroxycinnamic acid (CHCA); dihydroxybenzoic acid (DHB) isomers; trans-3,5-dimethoxy-4-hydroxycinnamic acid (SA); nicotinic acid; picolinic acid (PA); trans-3-methoxy-4-hydroxycinnamic acid (ferulic acid); 2,4,6-trihydroxyacetophenone (THAP); 2,6-dihydroxyacetophenone (DHA); 3-hydroxypicolinic acid (HPA); 3-aminoquinoline; trans-3-indoleacrylic acid (IAA); dithranol (DIT); 1,8,9-trihydroxy-anthracene; 2-(4-hydroxyphenylazo)-benzoic acid (HABA); 6-aza-2-thiothymine (ATT); 3-amino-4-methyl-5-nitropyridine (AMNP); 5-amino-1-naphthol (5,1-ANL); 5-hydroxy-1-naphthol (5,1-HNL); or a mix thereof.

10. The method according to claim 1, wherein the solution of step (c) further comprises an acid, the acid being selected from the group consisting of formic acid, trifluoroacetic acid or phosphoric acid at 0.05-1% v/v, and acetic acid or chlorhydric acid at a concentration ranging from 0.01-0.2 mol/L.

11. The method according to claim 1, said method comprising the step of:
    h. acquiring a full scan mode mass spectrum of ions on at least two areas present within a dried fluid spot, a first area being closer to a center of said dried fluid spot relatively to a second area,
    i. selecting mass-to-charge ratio (m/z) ions corresponding to a calculated mass-to-charge ratio of at least one compound to be detected in the said dried fluid spot,
    j. determining a spatial distribution of at least one compound within the dried fluid spot.

12. The method according to claim 11, wherein at least two dried fluid spots are provided, and wherein the step (h) is realized on at least two areas of each different dried fluid spots provided, said method also comprising the step of:
    k. comparing the spatial distribution of the at least one compound to be detected between the different dried fluid spots provided.

13. The method according to claim 1, wherein said conductive surface is selected among the group consisting of an Indium Tin Oxide (ITO) coated glass side, a stainless steel plate or a gold-coated plate.

14. The method according to claim 1, wherein the step (d) of the method is realized by spraying of said UV-light-absorbing compound by a manual airbrush, an automatic spray, a pneumatic spray or a mix thereof.

15. The method according to claim 1, wherein the compound to be detected is selected from the group consisting of nucleotides, amino acids, organic acids, carbohydrates, lipids, urea, and myo-inositol, said compounds being present in a body metabolome, drug candidates and pharmaceutical candidates.

* * * * *